(12) United States Patent
Potrepka et al.

(10) Patent No.: US 9,013,191 B2
(45) Date of Patent: Apr. 21, 2015

(54) MICROWAVE CAVITY WITH DIELECTRIC REGION AND METHOD THEREOF

(75) Inventors: Daniel M. Potrepka, Silver Spring, MD (US); Steven C. Tidrow, Edinburg, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 832 days.

(21) Appl. No.: 13/230,108

(22) Filed: Sep. 12, 2011

(65) Prior Publication Data

US 2013/0063158 A1    Mar. 14, 2013

(51) Int. Cl.
- *G01R 27/02* (2006.01)
- *G01R 27/26* (2006.01)
- *G01N 22/00* (2006.01)

(52) U.S. Cl.
CPC ............ *G01R 27/2658* (2013.01); *G01N 22/00* (2013.01)

(58) Field of Classification Search
CPC .............................. G01N 22/00; G01N 27/221
USPC .................. 324/632, 633, 636, 637, 639, 642
See application file for complete search history.

(56) References Cited

U.S. PATENT DOCUMENTS

| | | | | |
|---|---|---|---|---|
| 2,907,962 | A * | 10/1959 | Jaffe | .............................. 333/222 |
| 3,691,454 | A | 9/1972 | Hrubesh et al. | |
| 4,691,179 | A | 9/1987 | Blum | |
| 5,500,599 | A | 3/1996 | Stange | |
| 5,506,497 | A * | 4/1996 | Klein et al. | .................. 324/71.6 |
| 5,962,122 | A | 10/1999 | Walpita et al. | |
| 6,020,800 | A * | 2/2000 | Arakawa et al. | .............. 333/208 |
| 6,173,604 | B1 * | 1/2001 | Xiang et al. | ..................... 73/105 |
| 6,231,919 | B1 | 5/2001 | Craton | |
| 6,605,949 | B2 | 8/2003 | Heidinger et al. | |
| 6,864,690 | B1 | 3/2005 | Tidrow et al. | |
| 7,173,435 | B1 | 2/2007 | Fay et al. | |
| 2001/0035795 | A1 | 11/2001 | Matsuura et al. | |
| 2002/0101491 | A1 | 8/2002 | Ervin et al. | |
| 2003/0038633 | A1 | 2/2003 | Hyde | |

(Continued)

OTHER PUBLICATIONS

Stuart J. Penn, et al., High Q Dielectric Resonators using YBa2Cu3Ox Thick Films and Polycrystalline Dielectrics, IEEE Transactions on Applied Superconductivity vol. 7, No. 2, Jun. 1997 pp. 3500-3503.*

(Continued)

*Primary Examiner* — Melissa Koval
*Assistant Examiner* — Daniel Miller
(74) *Attorney, Agent, or Firm* — Lawrence E. Anderson

(57) ABSTRACT

A method and apparatus for obtaining dielectric constant and other measurements of a sample, comprising an open cavity resonator; a microwave energy generator for creating a resonating microwave in the open cavity resonator; a predetermined dielectric material having a high dielectric constant in the range of 2 to 100,000 substantially filling the region in which a microwave resonates; the dielectric material adapted to receive a sample for measurement of the dielectric properties of the sample; whereby during operation the resonating microwave beam is substantially immersed in the predetermined dielectric material such that the effective electrical spot size and beam cross-section along the cylindrical axis of the resonating microwave is reduced as a function of the inverse of the square root of the predetermined dielectric material dielectric constant. The dielectric constant or loss tangent of the sample may be determined based upon the change in the cavity's resonant frequency modes.

20 Claims, 5 Drawing Sheets

(56) References Cited

U.S. PATENT DOCUMENTS

| | | | |
|---|---|---|---|
| 2003/0146796 | A1 | 8/2003 | Matsuura et al. |
| 2004/0026028 | A1 | 2/2004 | Kirsten et al. |
| 2004/0085077 | A1 | 5/2004 | Nyfors |
| 2004/0134431 | A1 | 7/2004 | Sohn |
| 2004/0244501 | A1 | 12/2004 | Nyfors |
| 2005/0032233 | A1 | 2/2005 | Gopalsami et al. |
| 2005/0139063 | A1 | 6/2005 | Reininger |
| 2005/0145339 | A1 | 7/2005 | Matsuo |
| 2005/0179443 | A1* | 8/2005 | Peters et al. ............ 324/636 |
| 2006/0231756 | A1 | 10/2006 | Xiang et al. |
| 2006/0285108 | A1 | 12/2006 | Morrisroe |
| 2006/0286492 | A1 | 12/2006 | Morrisroe |
| 2007/0018657 | A1 | 1/2007 | Nagata et al. |
| 2008/0116903 | A1 | 5/2008 | Koerber |
| 2008/0128411 | A1 | 6/2008 | Martinez |
| 2008/0164874 | A1 | 7/2008 | White et al. |
| 2008/0173810 | A1 | 7/2008 | Morrisroe |
| 2009/0115416 | A1 | 5/2009 | White et al. |
| 2009/0140751 | A1 | 6/2009 | Takeuchi et al. |
| 2009/0195160 | A1 | 8/2009 | Shinogi |
| 2009/0230962 | A1 | 9/2009 | White et al. |
| 2009/0302866 | A1 | 12/2009 | Xiang et al. |
| 2009/0302956 | A1 | 12/2009 | Matsuura |
| 2010/0043976 | A1 | 2/2010 | Watanbe et al. |
| 2010/0320379 | A1 | 12/2010 | Morrisroe |
| 2011/0025328 | A1 | 2/2011 | Elliott |

OTHER PUBLICATIONS

A.L. Cullin and P.K. Yu, "Measurement of Permittivity by means of an open resonator: I. Theoretical," Proc. R. Soc. London A vol. 380, p. 49 (1982).

A.L. Cullin and P.K. Yu,"Complex source-point theory of the electromagnetic open resonator," Proc. Roy. Soc. London, Series A vol. 366, 165-171 (1979).

A.L. Cullin, et al., "Improvement in Open-resonator Permittivity Measurement," Electron Lett. vol. 8, 577-579 (1972).

A.L. Cullin and P.K. Yu, The accurate measurement of Permitivity by means of an open resonator, Proc. R. Soc. London A vol. 325, p. 493-504 (1971).

Eugene Hecht and Alfred Zajac, Optics, Addison Wesley. Reading MA (1976) p. 485.

Amnon Yariv, "Propagation of Optical Beams/Homogenous & Lens-like Media," Quantum Electronics, 3rd Edition, Wiley (NY) p. 118 (1989).

Mohammed N. Afsar and Kenneth J. Button, "Millimeter-Wave Dielectric Properties of Materials" in "Infrared and Millimeter Waves," vol. 12, Academic Press (1984). pp. 1-42.

Henry S.-W. Hu and James R. Griffith, "Synthesis and Structure-property Relationships of Low-dielectric constant Flourinated polyacrylates," Topics in Applied Chemistry: Fluoropolymers I: Synthesis, edited by Hougham et al., Plenum Press, NY (1999), pp. 167-180.

Dielectric Properties of Polymers, Zeus Technical White Paper (2005).

Zwick,Thomas et al., "Determination of the complex Permittivity of packaging materials at millimeterwave frequencies," IEEE Transactions on Microwave Theory and Techniques vol. 54, p. 1001-1010 (2006).

Harbarth et at., Confocal Fabry Perot microwave resonator at 48 GHz for high resolution $pectroscopy, J. Phys. E: Sci. Instrum. vol. 20. p. 409 (1987).

A. C. Lynch, Measurement of Permitivity by means of an open resonator, Proc. R. Soc. London A vol. 380, p. 73 (1982).

J.S. Yoon and D.C. Park, "Development of a liquid stub tuner for the KSTAR ICRF system," Applied Physics,vol. 7, Issue 3, Mar. 2007, pp. 314-317.

Roben E. Huie et al., "Effect of Bromine Substitution on the Lifetimes and Ozone Depletion Potentials of Organic Compounds," Physical and Chemical Properties Division, National Institute of Standards and Technology (NIST) Technical Publication 99F, Jun. 1, 2002.

Mohamed S. El-Genk, et al., "Saturation boiling of HFE-7100 from a copper surface, simulating a microelectronic chip," International J. of Heat and Mass Transfer vol. 46 Iss. I10, pp. 1841-1854 (2003).

Low-Loss Dielectric Materials Chan.J.mp:i/www.ccco:-;orb.com/sales Dielectric Chart.pdf.

Richard R. Thomas, Material Properties ofFluoropolymers, Topics in Applied Chemistry, Fluoropolymers 2—Properties, Edited by Gareth Hougham et al.. Springer US (2002), pp. 47-67.

Braakman, et al, "Principles and promise of Fabry—Perot resonators at terahertz frequencies," Journal of Applied Physics 109, 063102 (Mar. 2011).

Iryna Golovina, et al., New ceramic EPR resonators with high dielectric permittivity, Journal of Magnetic Resonance 195 (2008) 52-59.

* cited by examiner

MICROWAVE CAVITY WITH DIELECTRIC REGION AND METHOD THEREOF

GOVERNMENT INTEREST

The invention described herein may be manufactured, used, and/or licensed by or for the United States Government.

BACKGROUND OF THE INVENTION

Accurate determination of microwave material permittivity and loss factor over the entire microwave regime and over the desired temperature range of operation are needed for accurate design, operation and evaluation of microwave components, circuits, antenna and systems. Microwave engineers can input such precise material parameters into currently available software programs to accurately model devices as functions of temperature. In this way, the number of iterations and time required to develop components, circuits, subsystems and systems that operate to the specified performance level and over the specified temperature range of operation can be reduced. Such efficient development, rather than development by trial and error, will lower component, circuit, subsystem and system cost.

U.S. Pat. No. 6,864,690, hereby incorporated by reference, discloses an open confocal resonator-based system that allows for the accurate determination of microwave dielectric properties at multiple (25 to 50) frequency points in the frequency range 15 to 50 GHz and over the temperature range −50 to 125° C. Precision micrometer drive units are provided to move the sample about a vertical axis, to tilt the sample, and to move the sample in X, Y and Z directions. The drive units are positioned on a bearing slide for ease of sample positioning into and out of the cavity. Selected drive units are controllable from a remote location so that the apparatus may be utilized in an environmental chamber whereby measurements may be accomplished without opening the chamber after each measurement. All components of the resonator system, positioning units, cables, etc. are chosen such that they are operable over the desired temperature range of operation. However, the disclosed system has some significant limitations. The lower frequency limit (cut-off) due to physical constraints of the cavity and sample size is limited by cross-sectional area of the microwave mode supported by the cavity, the mode becoming prohibitively large at lower frequencies.

SUMMARY OF PRESENT INVENTION

The present invention relates to microwave measurements in an open confocal cavity resonator. A dielectric material of relatively high dielectric constant replaces the normal air or vacuum filled volume of the open cavity resonator; the region in which a cylindrically symmetric microwave resonance mode or beam is excited. This modification creates two improvements in the system. The size of the resonator can be reduced when using the same wavelength regime as for the regular size cavity with air/vacuum as the ambient medium and still maintain an adequate Q-value for the resonator. Alternatively, if the cavity size is maintained, use of the higher dielectric constant increases the maximum wavelength (lowers the cutoff frequency) below (above) which the Q-factor is satisfactory. Another improvement afforded by the replacement of the air in the cavity with a relatively high dielectric constant material is that smaller samples can be measured because the higher dielectric constant decreases the diameter of the microwave beam at the region in which the sample to be measured is placed (referred to as the beam waist).

The limitations described above of lower frequency limit (cut-off) due to physical constraints of the cavity and sample size limited by cross-sectional area of the microwave mode supported by the cavity (the mode becoming prohibitively large at lower frequencies) may be reduced and/)r overcome in accordance with the principles of the present invention by replacing the air-filled cavity with a solid (or liquid) filler medium having appropriate dielectric constant and microwave loss tangent. The boundary conditions of the cavity (two concave circular-spherical mirrors facing each other along a common cylindrical axis) define the resonant modes The $TEM_{00q}$ modes are used for measurement and allow for both isotropic and anisotropic dielectric property determination of a sample. The sample, which when centered in the cavity and oriented perpendicular to the cylindrical axis should be uniform in thickness within the beam waist region, is preferred from symmetry to be in the shape of a thin-circular disk for ease of operation and determination of dielectric constant. The test or sample material's dielectric constant and loss tangent are determined by the change in the unloaded cavity's $TEM_{00q}$ resonant frequency modes and their associated Q's, due to loading the cavity with the test material. Furthermore, the dielectric properties may he determined as a function of temperature by placing the cavity within an environmental chamber.

BRIEF DESCRIPTION OF THE DRAWINGS

The present invention can best be understood when reading the following specification with reference to the accompanying drawings, which are incorporated in and form a part of the specification, illustrate alternate embodiments of the present invention, and together with the description, serve to explain the principles of the invention. In the drawings.

Figure 1:
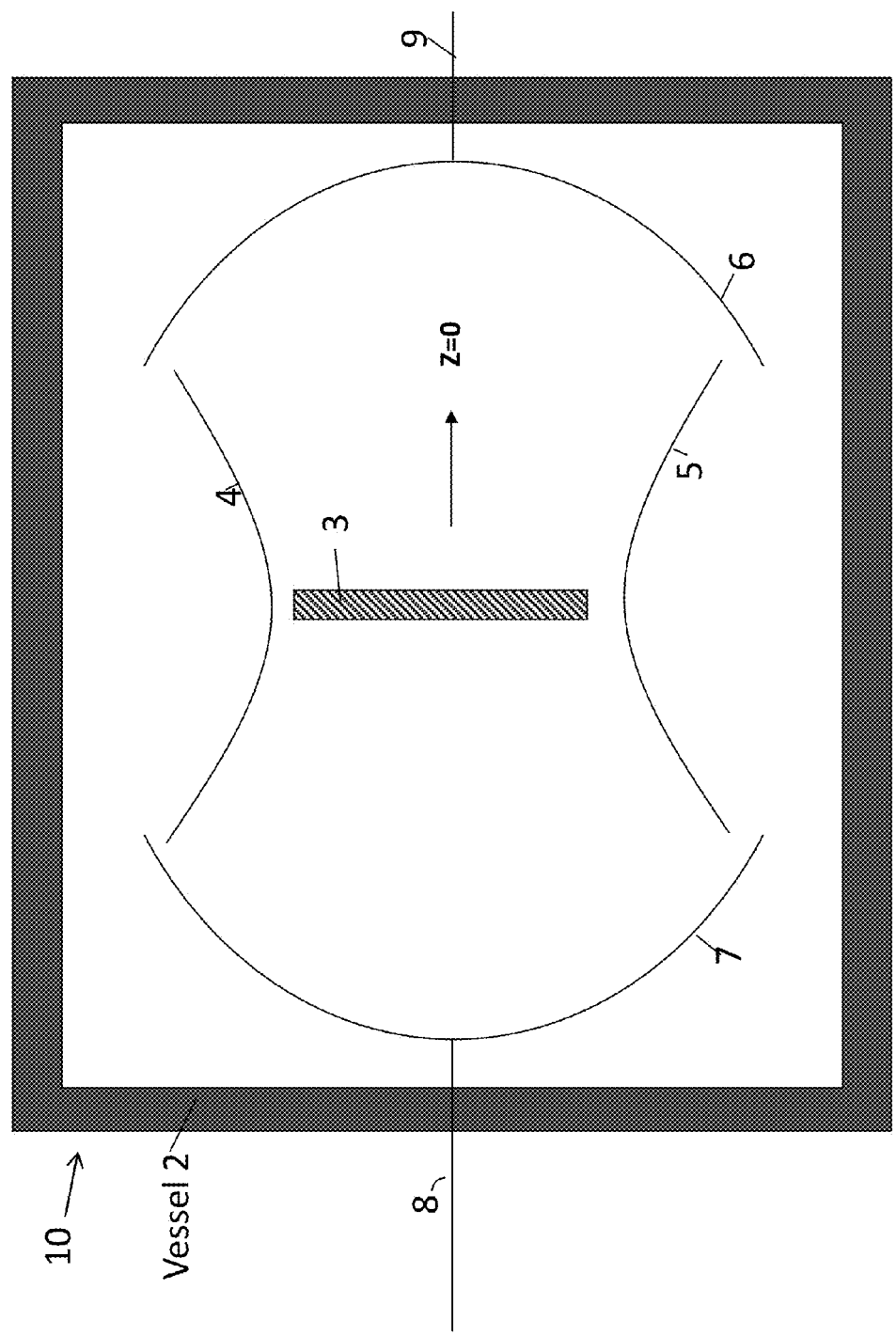
FIG. 1 is a schematic illustration of an open cavity resonator immersed in a relatively high dielectric constant filler material (liquid or solid) with sample (hatched cross-sectional area) placed in sample region centered on the cylindrical axis at z=0, and vessel (solid lines) surrounding the cavity region to contain liquid dielectric filler or gel-like dielectric filler materials.

A more complete appreciation of the invention will be readily obtained by reference to the following Description of the Preferred Embodiments and the accompanying drawings in which like numerals in different figures represent the same structures or elements. The representations in each of the figures are diagrammatic and no attempt is made to indicate actual scales or precise ratios. Proportional relationships are shown as approximates.

DETAILED DESCRIPTION OF THE PREFERRED EMBODIMENTS

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. In the drawings, the thickness of layers and regions may be exaggerated for clarity. Like numbers refer to like elements throughout. As used herein the term "and/or" includes any and all combinations of one or more of the associated listed items.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, components, regions, layers and/or sections, these elements, components, regions, layers and/or sections should not be limited by these terms. For example, when referring first and second locations, these terms are only used to distinguish one location, element, component, region, layer or section from another location, elements, component, region, layer or section. Thus, a first location, element, component, region, layer or section discussed below could be termed a second location, element, component, region, layer or section without departing from the teachings of the present invention.

Embodiments of the present invention are described herein with reference to cross-section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. The regions illustrated in the figures are schematic in nature and their shapes are not intended to illustrate the precise shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is an illustration of an open cavity resonator immersed in a relatively high dielectric constant filler material (liquid, gel or solid), with sample 3 (hatched) placed in sample region centered on the cylindrical axis at z=0, and vessel 2 surrounding the cavity region to contain liquid dielectric filler material. The curved borders 4, 5 above and below the sample represent extent of the solid filler material (containment vessel unnecessary in solid case). The z-axis is along the center of cylindrical symmetry with origin equidistant between the mirrors. The mirrors are represented by the curved surfaces 6, 7 on the left and right. The horizontal segments 8, 9 on the cylindrical axis represent the microwave feeds.

The well established open confocal resonator cavity theory that presently only accounts for a vacuum (air) filled cavity is modified to replace the "air" region with an arbitrary dielectric material so that the accurate dielectric properties of samples under test may be determined. The solutions, coded and packaged into a software program, allow the operator to easily determine the dielectric properties of materials under test.

Teflon, a relatively inexpensive, easily-machined, low-loss dielectric with dielectric constant of about 2.1 and available in large area and volume is used to fabricate and demonstrate the principles of the dielectric filled cavity. Alumina and other not so easily machined, but extremely low-loss dielectrics with dielectric constant of 10 or higher are used to fabricate a confocal cavity that should ultimately extend the frequency range of operation of the confocal resonator system to around C-band; thus, allowing sufficient characterization of numerous materials for communications applications.

The system performs a measurement of dielectric constant and loss tangent from resonance condition for given sample thickness t (sample-in, sample-out) using the relatively high dielectric constant material as the ambient medium in place of air.

Cavity size is constrained by beam waist and frequency range of interest. Other criteria include factors such as reduction in frequency, increase in wavelength of the microwave energy, desired reduction in diameter of sample while still maintaining a high Q-factor, and on desired cavity dimensions.

Possibilities for types of cavity mirrors include but are not limited to spherical, cylindrical, flat or any other shape of cavity mirrors and mirrors curved in such a way as to reduce or eliminate diffraction error, improve quality Q-factor, reduce losses for best tradeoff between convenience and performance giving satisfactory sensitivity and frequency range for the cavity system.

The measurement process involves a reference measurement without any sample in the cavity region (unloaded condition) and then a sample measurement (loaded condition) with the sample placed at the center of symmetry between the mirrors at the beam waist. For the loaded condition, samples must be inserted into position and removed afterward using a sample loading/unloading scheme. If a sample is to be measured in a solid medium, the sample must fit into a predetermined open slot that fits the sample into the region of the resonator volume, centered at the beam waist, allowing it to be surrounded by the ambient solid filler medium. For the reference measurement, a piece of the ambient solid "filler" material is fit into the empty slot (sample region) and measurements made. An open sample-sized slot is made in a region at the center of symmetry of the mirrors of the filled cavity resonator into which is placed:

1. a solid piece of material of the same type as in the rest of the cavity/tank—"filler" region, with dimensions that allow it to fill the open slot so that "reference measurements" may be made,
2. the sample of interest which is also the same size as the slot hole—is to be placed into the slot hole and measured, the data compared to the reference condition so that relative permittivity, loss, and permeability properties may be obtained.

The surrounding tank/containment-vessel for the volume of the liquid (or solid) dielectric has dimensions tailored to the cavity, so as to enhance total internal reflection, improving the Q of the cavity. The tank used for liquids (or gels) is shaped and composed of material liquid interface which optimize internal reflections.

The use of solid or liquid materials of relatively high dielectric constant as the cavity filler is proposed. The dielectric acts as the atmosphere in place of air or vacuum in the open cavity resonator volume. If the medium is a liquid, a tank needs to be put in place to contain the liquid and the cavity resonator, into which the sample would be lowered for measurements.

In the case of a liquid dielectric medium in the ambient cavity region as held by the containment vessel, reference measurements are made for the "empty or unloaded cavity condition" with cavity immersed in the tank of the dielectric medium and no sample in place. For the sample measurement, the sample is held in place at the center of symmetry of the cavity. A mechanism is provided to lower/slide the sample into the liquid-filled tank at the sample measurement position (located at the center of symmetry of the mirrors, at the beam waist) in order to make measurements for the loaded cavity case, and to later remove/retrieve it from the cavity once measurements are completed. The device to do this may consist of microwave-transparent "guide wires" or "guiding rods" attached to a holder that contains the sample, the holder being able to slide down and/or along the guiding wires or rods. The holder containing the sample can be slid into position so that the sample can be measured while at the center of the cavity. The immersed ends of the rods or wires can be fitted with stops such as enlarged ends that limit the sample and holder to the nominal measurement position. After the measurement is completed, the sample in the holder can then be slid up or out along the guide wires (rods), removing the sample from the cavity.

Bean Waist Physics for Dielectric-Filled Cavity

From Gaussian Beam Theory, for an open resonator with mirror separation D in vacuum or air ambient ($\in=1$), $d=D/2-t$, and dielectric sample with half thickness t and refractive index n placed at the beam waist, as referenced in A. L. Cullin and P. K. Yu, "The Accurate Measurement of Permittivity by Means of an Open Resonator," Proc. R. Soc. London A Volume 325, p. 493 (1971) (hereby incorporated by reference), an expression defining the beam waist can be written as $$Kw_o^2 = 2[(d+t/n^2)(R_o-d-t/n^2)]^{1/2} \quad (1)$$

$$K = 2\pi/\lambda \quad (2)$$

where $\lambda$ is the where A is the microwave radiation wavelength of frequency f. Consider the case for an empty cavity (no sample). Then $t \to 0$. If the resonators are confocal, as referenced in Eugene Hecht, et al., Optics, Addison Wesley, Reading Mass. (1976) p. 485, then, by definition, $R_o=D$. In addition, allow the ambient medium to have variable dielectric constant, so that $\lambda \to \lambda/\in^{1/2}$. Then for a confocal cavity immersed in dielectric medium of dielectric constant $\in$ and containing no sample, Equation 1 becomes $$w_o^2 = \lambda R_o/2\pi \in^{1/2} \text{ (Cavity with } R_o \sim D, \text{ medium } \in, \text{ no sample).} \quad (3)$$

The cavity to use in this application deviates from the confocal condition, having $R_o$ smaller than D (equal to 2D/3) which reduces diffraction losses compared to the strict definition of the confocal resonator. If a cavity resonator with this condition is immersed in a dielectric medium with dielectric constant $\in$ and contains no sample, Equation 1 becomes $$w_o^2 = 3^{1/2} \lambda R_o/4\pi \in^{1/2} \text{ (Cavity with } R_o \sim 2D/3, \text{ medium } \in, \text{ no sample).} \quad (4)$$

Figure 2:
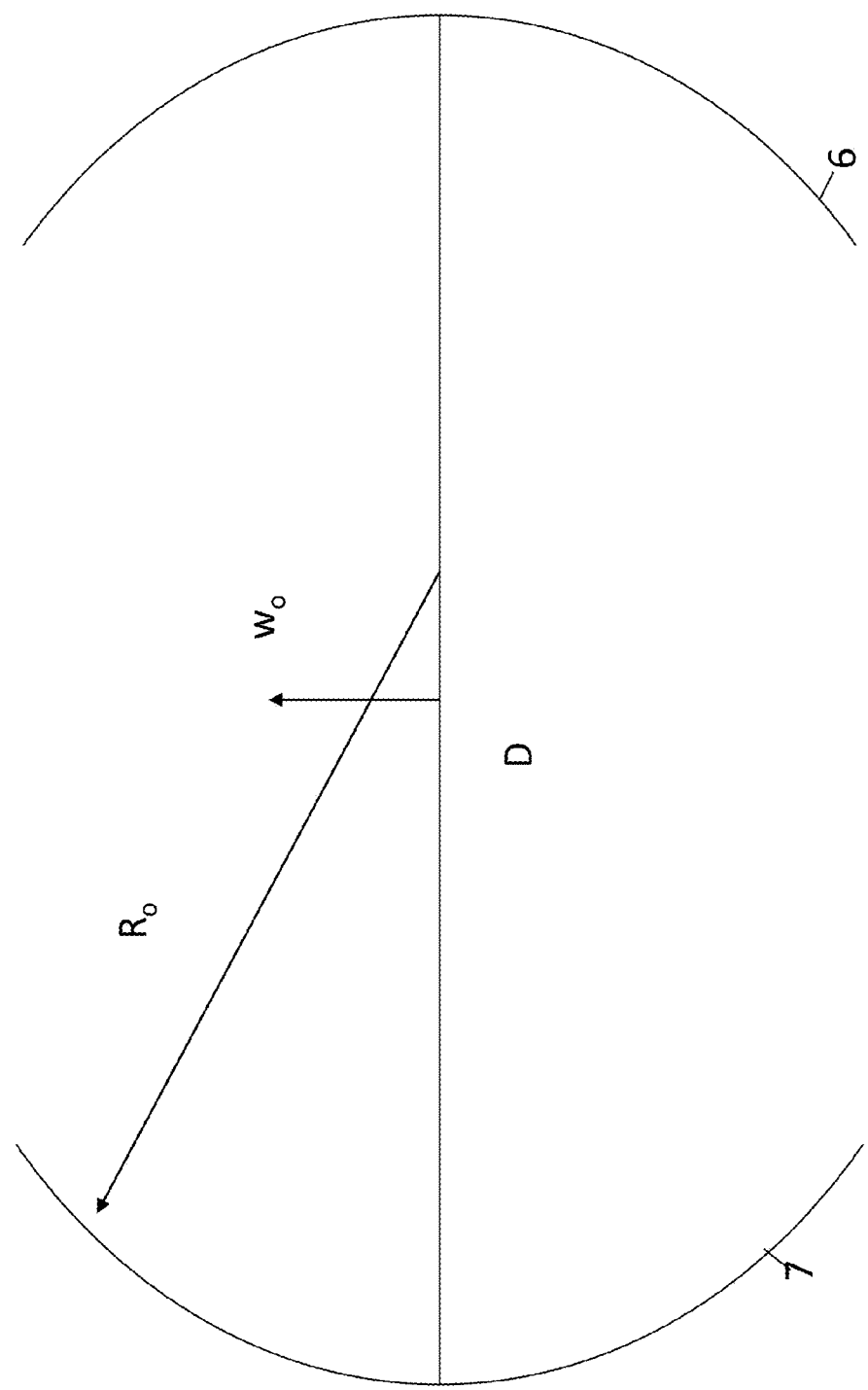
FIG. 2 is a schematic illustration of an open resonator with mirrors 6, 7 whose radii of curvature are $R_0$ with mirror separation distance 2$d$, so that cylindrically symmetric microwave-beam mode excited in it focuses down to a minimum beam size (of circular symmetry) at z=0, the beam at z=0 having radius of $w_o$ (spatial dimension) defined as the beam waist.

From the geometry of the cavity resonator (FIGS. 1 and 2), one can see that the size of the beam waist radius, $w_0$, constrains the combination of mirror size and distance between mirrors, 2d, for which an adequate quality factor (Q-factor) of the cavity resonator may be achieved. Extending this geometric argument, if the dielectric constant of the ambient medium, $\in$, could be increased, this would allow the size of the beam waist radius to be smaller, scaling down cavity size (mirror separation and radius of curvature) in accordance with Equation 3 or 4, allowing use of a smaller sample size in the beam waist region too but still maintaining high Q-factor. Considering frequency dependence instead of or in addition to cavity-size reduction, the larger dielectric constant medium reduces beam waist size at higher frequencies (shorter wavelengths).

Figure 3:
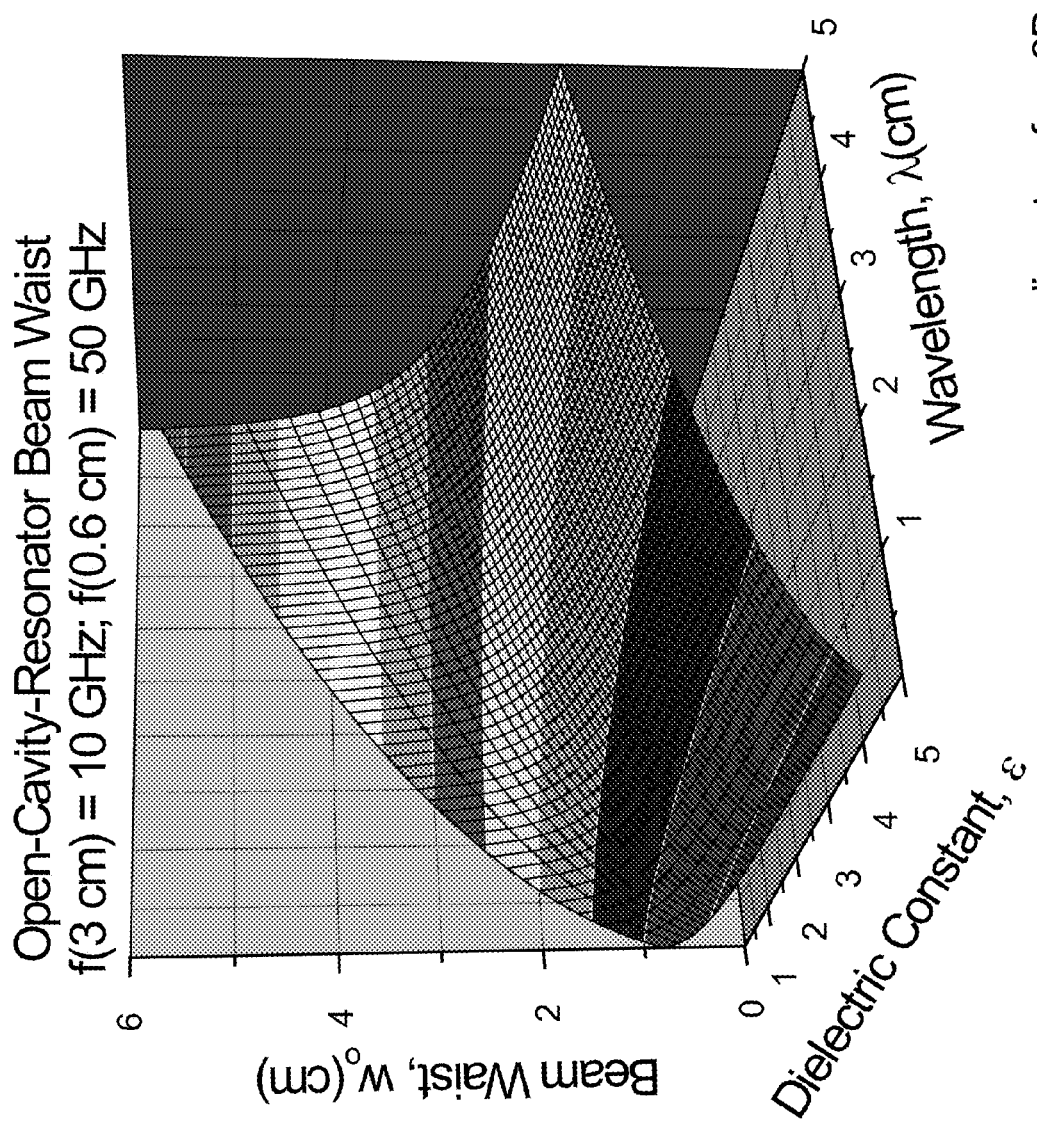
FIG. 3 graphically illustrates beam waist, $w_0$, as a function of both the dielectric constant, $\in$, and the microwave excitation frequency, f; (wavelength, $\lambda$=c/f, where c=speed of light).

For a cavity resonator, $R_o=6"$, $D=9"$, 10 GHz<f<50 GHz, 0.6 cm<$\lambda$<3 cm, see FIG. 3, depicting measured results for an Open-Cavity-Resonator Beam Waist f(3 cm)=10 GHz; f(0.6 cm)=50 GHz By doubling the dielectric constant, the beam waist shrinks by about 16% and by quintupling it shrinks by 33%. Assuming apparatus size scales roughly with beam waist, similar shrinkage is expected in the size of the apparatus, from 9" plate separation to 6" for dielectric constant 5. The 6.625" diameter mirror plate scales down to 4.4" diameter, but scaling down the radius of curvature of the mirrors to 3" (based on what the scaled-down plate separation would accommodate) gives plate diameter of about 3.5 in.

Quality Factor for Dielectric Filled Cavity

U.S. Pat. No. 6,864,690, hereby incorporated by reference, discloses an open confocal resonator-based system that allows for the accurate determination of microwave dielectric properties at multiple (25 to 50) frequency points in the frequency range 15 to 50 GHz and over the temperature range −50 to 125° C. However, the system disclosed therein has some significant limitations. The lower frequency limit (cutoff) due to physical constraints of the cavity and sample size is limited by cross-sectional area of the microwave mode supported by the cavity, the mode through beam waist becoming prohibitively large at lower frequencies. These limitations may be reduced and/or overcome in accordance with the principles of the present invention by replacing the air-filled cavity with a solid (or liquid) filler medium having appropriate dielectric constant and microwave loss tangent.

The boundary conditions of the cavity (two concave circular-spherical mirrors facing each other along a common cylindrical axis) define the resonant modes. The TEMoog modes are used for measurement and allow for both isotropic and anisotropic dielectric property determination of a sample (in the shape of a -circular dielectric test material) which may be centered in the cavity and oriented perpendicular to the cylindrical axis. The test material's dielectric constant and loss tangent are determined by the change in the unloaded cavity's TEMoog resonant frequency modes and their associated Q's, due to loading the cavity with the test material. Furthermore, the dielectric properties may be determined as a function of temperature by placing the cavity within an environmental chamber. Gaussian-beam and open confocal resonator theories show that the radius of the microwave beams cross-section at the midpoint between the mirrors where the sample is placed (beam waist) limits minimum sample size (see Beam Waist Physics Section). A dielectric-filled cavity is advantageous because the beam waist decreases with increasing dielectric constant compared with an air-filled (or evacuated) open cavity, scaling inversely with the fourth- root of the dielectric constant of the filler material. With the microwave beam now immersed in the dielectric, the "effective" electrical spot size and beam cross-section anywhere along the cylindrical axis (nominally proportional to the beam waist squared), is a function of the inverse of the square root of the dielectric constant. Cavity volume occupied by the beam shrinks with increasing dielectric constant of the filler material. In addition, the wavelength of microwaves inside the dielectric medium is smaller than in air (allowing the cavity to support modes above the wavelength limit in air, i.e. for lower frequencies than are possible in air). Whereas the air-filled cavity is truly an open cavity from which microwaves can escape, the solid (liquid) tiller can be shaped (or bounded by a shaped container in the liquid case) to occupy only the region between the mirrors and has a cylindrically- symmetric boundary with air that improves containment of the standing-microwave mode between the mirrors through internal reflection. Together these phenomena serve to increase the energy density in the dielectric medium relative to the air-filled case, raising the Q of the cavity. Hence a dielectric-filled confocal resonator system, reduces sample size (a key to reducing the cost when developing new materials) and may provide frequency and temperature-dependent dielectric properties of materials in the X—band frequency regime where it has heretofore been difficult to fully characterize microwave materials for communication systems.

Cut-Off Frequency

The cutoff frequency is that minimum frequency that satisfies the equation $$f/f_0 = (q+1) + [(2p+l+1)/\pi]\arccos(1-D/R_0) \quad (5)$$

where, $f_0 = c/2D\in^{1/2}$. For the cavity resonator with 2D=9 in.× 254 cm/in. and for the q=1 mode, Equation (5) becomes:

$$f = f_0(q+1)|_{q=1} = c/2D\in^{1/2} = 1.312335958 \text{ GHz}/\in^{1/2} \quad (6)$$

Figure 4:
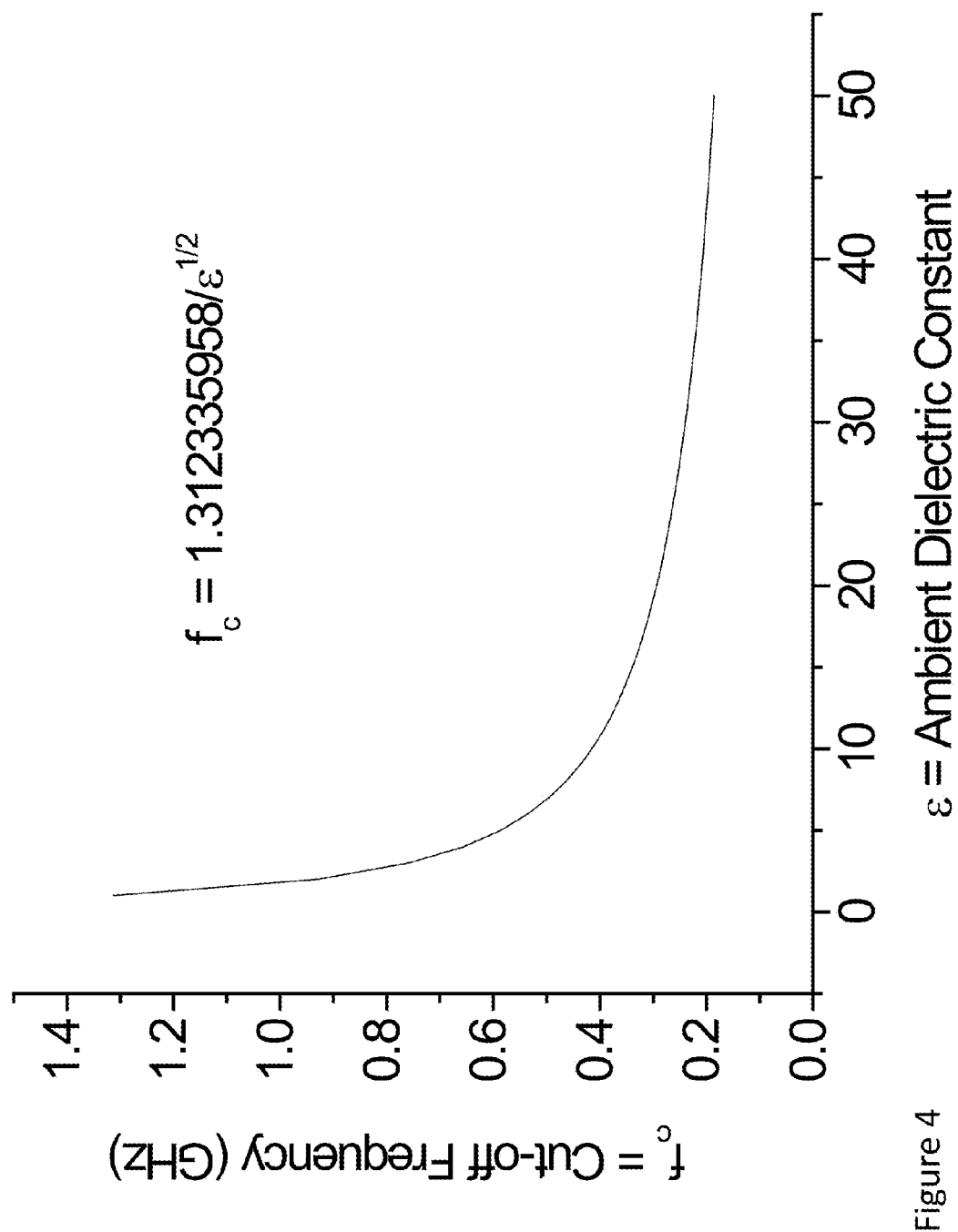
FIG. 4 graphically illustrates the dependence of cut-off frequency on ambient dielectric constant.

The graph in FIG. 4 shows that small increases in dielectric constant (from $\in=1$) would dramatically reduce the cut-off frequency of the open resonator.

Low Attenuation Criterion for Choosing the Filler Material $$\beta = \omega/c)[\in_r(1+i\tan\delta)]^{1/2} \quad (7)$$

For $\tan\delta \ll 1$ and $k = \omega\in_r^{1/2}/c$, $$E = E_0\exp(ikz)\exp(-k\cdot\tan\delta\cdot z/2) \quad (8)$$

$$P = |E|^2\exp(-k\cdot\tan\delta\cdot z/2) = E_0|^2\exp(-2\pi\cdot\tan\delta\cdot z/\lambda) \quad (9)$$

$$\text{Attenuation} = 2\pi\cdot\tan\delta/\lambda = \text{Figure of Merit}(FOM) \quad (10)$$

Candidate materials include any insulating material transparent to the frequency of interest with nominally high Q, relatively high dielectric constant, as shown by the figure of merit. Additionally, in researching the literature for candidate materials, the wavelength must be considered, because one must evaluate the attenuation as the figure of merit in order to accurately determine its promise as a background material, i.e. consider the ratio of tan·δ to λ, not just the loss tangent alone.

These phenomena (modifications of beam waist physics, changes in Q, potential lowering of cutoff frequency, and attenuation as a result of using a filler material with a given dielectric constant and loss in the appropriate microwave regime) are to be accounted for in the computer computational software to be used for data calculations.

Types of liquid relatively high dielectric constant materials would include nonpolar liquids with little solvent action, and low losses. See in this regard Mohammed, N., et al. Millimeter-Wave Detection Properties in Materials in "Infrared and Millimeter Waves," Vol. 12, pp 1-42, Academic Press (1984), p. 23, hereby incorporated by reference.

Examples of nonpolar liquids with low solvent action include:

3M Fluorinert ™ Liquids (ozone depleting potential)
Nominal Properties (depending on the formulation):
Temperature Range: −101° C. to 215° C.,
Dielectric Constant <1.72-1.98 (1 MHz)
Dissipation Factor <0.0005 (1 MHz)
Novec™ Hydrofluoroether (HFE) Engineered Fluids (global warming potential)
CFC substitutes
HFE-7100
Temperature Range: −135° C. to 60° C.,
Dielectric Constant=7.39 (100 Hz-10 MHz)
Dissipation Factor<0.0010 (1 MHz)
HFE-7500
Temperature Range: −100° C. to 128° C.
Dielectric Constant=5.8, 7.4 (1 kHz) http://www.acota.co.uk/products/Novec-Fluids
Frequency and Dissipation Factor not reported
At 1 kHz, Dielectric Constant=7.3-7.4 for HFE-7000, 7100, and 7200; Dielectric Constant=5.8 for HFE-7500.

Hu and Griffith, "Synthesis and Structure-property Relationships of low-dielectric—constant Fluorinated Polyacrylates, Flouropolymers 1: Synthesis, edited by Hougham et al., Plenum Press, NY (1999), pp. 167-180, hereby incorporated by reference, show that less free volume, lower entropy, increases dielectric constant. This trend correlates with higher percent fluorine.

Solid dielectrics that can be molded and shaped or cut into pieces that are inserted and self-aligned relative to sample and cavity faces can also be used for the ambient dielectric filler material in the cavity. Examples of candidate solid-dielectric materials include the non-polar plastics. They are truly covalent with symmetrical molecular structures, no polar dipoles, and slight instantaneous movement of electrons (electronic polarization) in response to the E-field, with high resistivity and dielectric constant fairly independent of ac frequency because electron polarization is instantaneous. See "Dielectric Properties of Polymers, Zeus Technical White Paper (2005), hereby incorporated by reference. Other candidates include solids with even higher dielectric constants, such as low loss quartz and the material shown in the table. Non-polar plastics typically have dielectric constants $2 \leq \in \leq 3$, while dielectric constants as high as 10 occur for such standard materials as sapphire and glass as reported in Low-Loss Dielectric Materials Chart, Http://www.eccosorb.com/sales/Dielectric Chart.pdf, hereby incorporated by reference.

A dielectric is an electrical insulator that may be polarized by an electric field, which causes positive and negative charges within the dielectric to be displaced in opposing directions resulting in an electric field within the dielectric. The permittivity of the dielectric material depends on the frequency of the applied field for dielectric dispersion to occur. Permittivity is the measure of the resistance that is encountered when forming an electric field in a dielectric medium. Materials can be classified according to their permittivity ($\in'$ is the real part of the permittivity) and conductivity, σ. Materials with a large amount of loss inhibit the propagation of electromagnetic waves. When $\sigma/(\omega\in') \gg 1$, the material the material is considered to be a good conductor, where $\omega$ is the angular frequency of the applied field. Dielectrics are associated with lossless or low-loss materials, where $\sigma/(\omega\epsilon') \ll 1$. Dissipation Factor (D), Loss Tangent and tan $\delta$ are identical. The dielectric loss factor is the product of its dielectric constant and its dielectric loss tangent (or dissipation Factor). Lossy dielectrics may be characterized by a tan $\delta$ above approximately 0.1. Low-loss dielectrics are associated with a tan $\delta$ below 0.001 and include semiconductors, glass, and plastics.

Over the microwave range, dielectric properties vary relatively little with frequency. Homogeneous dielectric materials include porcelain, most plastics, glass, metal oxides, semiconductors (e.g., silicon) and pure single crystals. Solid dielectrics are perhaps the most commonly used dielectrics in electrical engineering, and many solids are very good insulators. Mineral oil is used extensively inside electrical transformers as a fluid dielectric. Mixtures of dielectric materials, or composite dielectrics, are combinations of dielectrics used to attain specific values for dielectric constants and loss tangents. In connection with the semiconductor process, a high-$\kappa$ dielectric refers to a material with a high dielectric constant $\kappa$ (as compared to 3.9 for silicon dioxide). Dielectric properties may be artificially adjusted with relatively conductive particles.

Examples of non-polar plastics include polytetrafluoroethylene or Teflon™ (PTFE) and many other fluoropolymers polyethylene (PE), polypropylene (PP), and polystyrene (PS)

| Polymer | Frequency | Diel. Const. | Loss tangent/f (Hz) | Source |
| --- | --- | --- | --- | --- |
| PTFE | 1 MHz | 2.0-2.1 | $3\text{-}7 \times 10^{-9}$ | Goodfellow |
| PE | 1 MHz | 2.2-2.35 | $1\text{-}10 \times 10^{-10}$ | Goodfellow |
| PP | 60 Hz | 2.2-2.6 | $5\text{-}8.3 \times 10^{-6}$ | Goodfellow |
| PS* | 1 MHz | 2.5 | $2 \times 10^{-10}$ | Goodfellow |
| PS | 1 MHz-500 GHz | 2.53 | $1.2 \times 10^{-10}\text{-}2.4 \times 10^{-16}$ | Rexolite |
| EGC-1700** | 1 kHz | 3.1 | $8.8 \times 10^{-6}$ | 3M |

*Cross-Linked,
**Novec ™ Electronic Coating EGC-1700

By precision construction, the self-alignment of sample, cavity mirrors, and filler materials of high dielectric constant and low loss can be achieved. Spurious dispersion effects that would otherwise occur at boundaries between individual pieces can be suppressed by shaping, fitting contact between pieces, accommodating pieces of varying dimensions and shapes to be fit together in the cavity with or without a sample present, molding pieces or filling in between with shims, and using organic fillers at interfaces with the ordinarily high-surface-tension surfaces of fluoropolymers such as referenced in Richard R. Thomas, Material Properties of Fluoropolymers, Topics in Applied Chemistry, Fluoropolymers 2—Properties, Edited by Gareth Hougham et al. Springer US (2002), pp. 47-67 (hereby incorporated by reference).

Inorganic Filler Materials

| Material | $e_r$ | TCf (ppm/K) | Loss Tan = 1/Q | f (GHz) |
| --- | --- | --- | --- | --- |
| Al$_2$O$_3$ (Ti doped) | 10 | −60 | $1.7 \times 10^{-5}$ | 9 |
| Ba (Mg$_{1/3}$Ta$_{2/3}$)O$_3$ | 24 | 0 | $3.8 \times 10^{-5}$ | 10 |
| Ba—Zn—Ta—O | 30 | −3 … 3 | $8.3 \times 10^{-5}$ | 6 |
| Zr—Sn—Ti—O | 38 | −3 | $1.25 \times 10^{-4}$ | 7 |
| Ca—Ti-RE-Me | 47 | 20 | $1.67 \times 10^{-4}$ | 6.5 |
| Ba—Nd—Ti—O | 80 | 90 | $4 \times 10^{-4}$ | 5.5 |
| TiO$_2$ | 100 | 450 | $5.9 \times 10^{-5}$ | 3 |

Figure 5A:
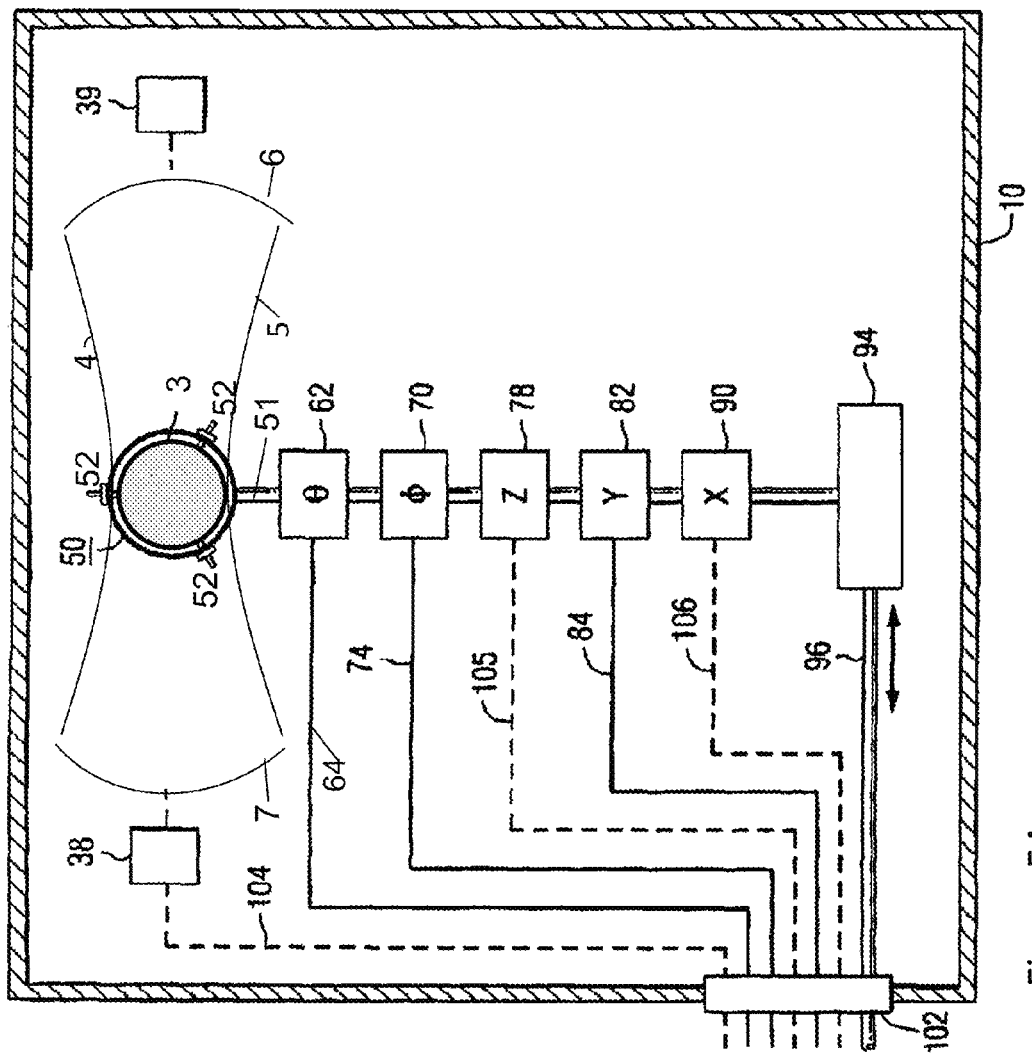
FIG. 5A is a schematic illustration of an apparatus embodying the principles of the present invention for obtaining dielectric constant, and other measurements, such as loss tangent, of a sample 3.
Figure 5B:
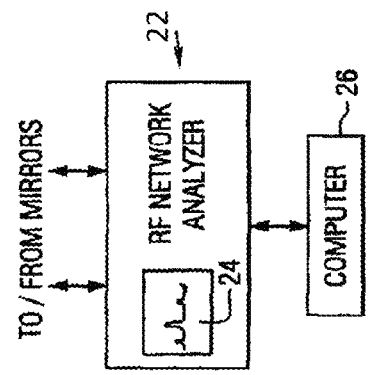
FIG. 5B is a schematic illustration of the computer and network analyzer.

FIG. 5 shows a schematic illustration of an apparatus for obtaining dielectric constant, and other measurements, such as loss tangent, of a sample 3. The sample 3 is positioned in the cavity 14 between two confocal mirrors 6 and 7, and is maintained in position between the mirrors by means of a fixture in the form of a sample holder 20 that is typically Teflon or other nonmetal material for parts of the sample holder disposed in the cavity 14. Metal parts such as rods and screws may also be used for parts of the sample holder that are disposed outside the cavity 14. Both of the mirrors 6 and 7 are supplied with microwave signals from an RF network analyzer 22 having a screen 24. Some of the microwave energy is reflected back to the network analyzer 22 from the inputs to the mirrors, while the remainder of the energy is transmitted to the opposed mirror where it is reflected and maintained in the resonant cavity for a period of time and thereafter provided to the network analyzer 22. The network analyzer 22 is operative to extract data from the received signals and provides the information to a computer 26 having a program for determining the desired values of the parameters being measured.

In most instances multiple measurements are made, both with a sample in the resonant cavity (loaded) and without the sample (unloaded), to obtain an average value with statistical errors for the parameters being measured. When making measurements on a sample, the operator performs a lengthy procedure for initializing the correct position, centering the uniform sample within the cavity.

The apparatus of FIG. 5A includes opposed confocal mirrors 6 and 7 positioned on respective mounting brackets, not shown. The mirrors 6 and 7 are precisely moveable toward and away from one another, along a Y direction, by means of drive units 38 and 39, such drive units being constituted by micrometer drives which have an accuracy of around 1/10,000 of an inch. Alternatively but not shown in the figure, cables can be connected to drive units 38 and 39, so that the length of the cavity can be controlled via manipulation from a remote location. For a more detailed description, see U.S. Pat. No. 6,862,690, hereby incorporated by reference.

A sample holder 50 is moveable into the cavity along an X direction, for allowing a sample to be inserted and withdrawn from the cavity. The sample holder 50 is in the form of a ring, supported by a shaft 51, and having an inside diameter DR, which is greater than the diameter DM of a confocal mirror 6 or 7. The holder is fabricated of a non-metallic material, such as plastic, so that no eddy currents are generated to interfere with the dielectric constant measurements. A series of adjustable metallic or non-metallic pins or screws 52 maintain a sample 3 in position for insertion into cavity.

Referring once again to FIG. 5A, it is seen that the shaft 51 of holder 50 is inserted into, and held by, a cylinder connected to a first drive unit 62. This first drive unit 62 is a precision micrometer drive which can rotate the cylinder resulting in the sample holder 50 being operably connected to the first drive unit 62 for rotation θ about a vertical axis. A cable 64 connected to drive unit 62, allows for precision control of θ from a remote location.

The holder 50 is operably connected to a second precision micrometer drive unit 70 via a platform (not shown) for tilt movement about a tilt axis such that the top of the holder 50 will move toward one mirror more than the bottom of the holder. A cable 74 connected to drive unit 70, allows for precision control from a remote location.

Vertical, or Z movement of the holder 50 is accomplished by its connection to a third precision micrometer drive unit 78, held by bracket (not shown) and connected to a platform (not shown) via the second drive unit 70. The Z drive unit 78 is initially adjusted by hand and in general will not require subsequent adjustment.

A critical and sensitive positioning of the sample is in the Y direction, that is, toward and away from a mirror while the sample is in the cavity. Accordingly, a fourth precision micrometer drive unit 82 is provided and is operable from a remote location by means of cable 84. This Y drive unit 82 is mounted on a platform (not shown) and is coupled to a bracket (described in further detail in U.S. Pat. No. 6,864,690).

A fifth precision micrometer drive unit 90 is operable to move the holder 50 in a horizontal X direction within the cavity for fine-tuning the X position during initial setup. All of the above noted precision micrometer drive units, along with holder 50 are collectively moved into and out of the cavity by means of a precision bearing slide 94, moveable by means of a rod 96 connected to an extension bracket secured to a platform (as described in further detail in U.S. Pat. No. 6,864,690).

The positioning of the bearing slide is extremely accurate such that after a measurement is taken on a sample and it is withdrawn, the sample may be repositioned in the exact same location as the previous measurement, particularly if the sample is relatively thick. For thinner samples the drive units may have to be activated for precision sample placement. The remote operation capability is particularly useful when measurements are made under different temperature conditions. For example, the chamber 10 may have a temperature range of, for example, −50° C. to 100° C. Bearing slide 94, which carries all of the drive units, as well as the sample, may be moved to a desired position whereby the sample is precisely located within the cavity. After the measurement is made, the sample may be withdrawn from the cavity and subsequently reinserted to the exact same position. All of this movement is accomplished from outside of the chamber 10 by pushing or pulling the rod 96.

The rod 96 extends out of the chamber 100 through an insulated aperture 102 which may also accommodate the cables 64, 74 and 84 from respective drive units 62, 70 and 82. and 82. As indicated by dotted lines 104, 105 and 106, drive units 38, 39, 78 and 90 may also, if desired, be provided with remotely operated capabilities.

With the arrangement of FIG. 5A the sample position can be initialized with facility and may be accurately repositioned after a reinsertion into the cavity, for tests at multiple temperatures. All of this is accomplished without the requirement to open the chamber after each measurement. Gross movement of the sample and drive units is accomplished by the rod 96 connected to bearing slide 94, while movement of selected drive units is accomplished by cables. Alternatively, such drive unit control may be by servo drives, suitably conditioned for low and high temperature operation.

As used in the following claims the terminology "sample" means the dielectric material for evaluation.

Although various preferred embodiments of the present invention have been described herein in detail to provide for complete and clear disclosure, it will be appreciated by those skilled in the art that variations may be made thereto without departing from the spirit of the invention.

It should be emphasized that the above-described embodiments are merely possible examples of implementations. Many variations and modifications may be made to the above-described embodiments. All such modifications and variations are intended to be included herein within the scope of the disclosure and protected by the following claims.

The invention claimed is:

1. An apparatus for obtaining a dielectric constant and other measurements of a sample, comprising:
an open cavity resonator;
a microwave energy generator for creating a resonating microwave in the open cavity resonator;
a predetermined dielectric material, the predetermined dielectric material being one of a liquid or gel having a high dielectric constant in the range of 2 to 100,000 substantially filling the region of the open cavity resonator in which a microwave resonates; the dielectric material adapted to receive a sample for measurement of the dielectric properties of the sample;
whereby during operation the resonating microwave is substantially immersed in the predetermined dielectric material such that an effective electrical spot size and beam cross-section along a cylindrical axis of the resonating microwave is reduced as a function of the inverse of the square root of the predetermined dielectric material dielectric constant.

2. The apparatus of claim 1 further comprising a sample holder moveable through the liquid or gel dielectric material in the open cavity resonator, and wherein the predetermined dielectric material is one of a liquid or gel, and wherein the microwave is cylindrically symmetric, and wherein the predetermined dielectric material fills the region in which the cylindrically symmetric microwave resonates.

3. The apparatus of claim 1 wherein the predetermined dielectric material configures the region of the open cavity resonator in which a microwave resonates to permit the same wavelength regime as for a standard size cavity and still maintain an adequate Q-value for the resonator, and wherein use of the high dielectric constant increases the maximum wavelength and lowers the cutoff frequency at which the Q-value is satisfactory for determining microwave dielectric properties and whereby smaller samples are measurable because the high dielectric constant decreases the diameter of the microwave beam at the region in which the sample to be measured is placed.

4. The apparatus of claim 1 further comprising a sample holder moveable through the liquid or gel dielectric material in the open cavity resonator allowing the sample to be inserted and withdrawn, the sample holder being formed of nonmetallic material so that no eddy currents are generated, and wherein the microwave energy generator comprises a pair of opposed confocal mirrors supplied with microwave energy; each of the opposed mirrors operable to provide corresponding microwave output signals for analysis to determine the dielectric constant and other measurements, and wherein the dielectric material occupies substantially only a region between the opposed confocal mirrors, the dielectric material having a substantially cylindrically symmetric boundary with air that improves containment of a standing microwave between the mirrors due to internal reflection.

5. The apparatus of claim 1 wherein the predetermined dielectric material has a loss tangent, and wherein the dielectric constant is in the range of 2 to 3.1 and the loss tangent is in the range of $1 \times 10^{-4}$ to $2 \times 10^{-10}$.

6. The apparatus of claim 1 further comprising a sample holder moveable through the liquid or gel dielectric material in the open cavity resonator allowing the sample to be inserted and withdrawn, the sample holder being formed of nonmetallic material so that no eddy currents are generated, and wherein the microwave energy generator comprises a pair of opposed confocal mirrors, and wherein the open cavity resonator has a cutoff frequency, and wherein the cutoff frequency is the minimum frequency that satisfies the equation $f/f_0=(q+1)+[(2p+l+1)/\pi]\arccos(1-D/R_0)$, where, $f_0=c/2D\in^{1/2}$, where f is frequency, $f_0$ is resonant frequency, $R_0$ is the radius of curvature of the confocal mirrors, D is the distance between centers of the confocal mirrors, q, p, l are mode indices which define the resonances of the cavity, and wherein the values of D are selected such that small increases in dielectric constant (from $\in=1$) dramatically reduce the cutoff frequency of the apparatus.

7. The apparatus of claim 1 further comprising:
at least one mirror;
a sample holder;
a first drive unit operatively connected to said holder to rotate said holder, with said sample, about a vertical axis through the liquid or gel dielectric material;
a second drive unit operatively connected to said holder to tilt said holder, with said sample, relative to the at least one mirror through the liquid or gel dielectric material;
a third drive unit operatively connected to said holder to move said holder, with said sample, along a vertical axis through the liquid or gel dielectric material;
a fourth drive unit operatively connected to said holder to move said holder, with said sample, along a first horizontal axis toward and away from the at least one mirror through the liquid or gel dielectric material;
a fifth drive unit operatively connected to said holder to move said holder, with said sample, along a second horizontal axis when in said cavity of said resonator through the liquid or gel dielectric material, said second horizontal axis being at a right angle with respect to said first horizontal axis;
a bearing slide;
said drive units being positioned on, and carried by said bearing slide which is moveable to position said holder into and out of said open cavity resonator.

8. The apparatus of claim 1 wherein the open cavity resonator has a quality factor associated therewith and wherein the dielectric material is a liquid and further comprising a containment vessel for containing the liquid dielectric material having dimensions tailored to the open cavity resonator so as to enhance total internal reflection and improve the quality factor Q of the cavity, and wherein the sample is movable through the liquid.

9. The apparatus of claim 8 further comprising a surrounding containment vessel and wherein surrounding containment vessel comprises a material liquid interface which optimizes internal reflections of microwaves.

10. The apparatus of claim 1 wherein the sample is held by microwave-transparent guide wires or guiding rods attached to a holder that contains the sample and wherein the holder is configured to be moved into and out of place by the guiding wires or rods through the liquid or gel dielectric material.

11. A method for obtaining a dielectric property or loss tangent of a sample, comprising:

providing an open cavity resonator assembly; the open cavity resonator assembly comprising two mirrors for the transmission of microwaves; the two mirrors facing each other along a common cylindrical axis forming a boundary of a cavity region defining resonant frequency modes;
selecting and placing in the cavity region a predetermined dielectric material; the dielectric material being one of a liquid or gel and having a dielectric constant in the range of 2 to 100,000;
inserting a sample into the region containing the predetermined dielectric material; the predetermined dielectric material substantially occupying the cavity region between the sample and the two mirrors;
providing a microwave energy generator for generating a resonating microwave in the cavity region;
determining one of the dielectric constant or loss tangent of the sample based upon a change in the cavity's resonant frequency modes.

12. The method of claim 11 wherein the predetermined dielectric material is a liquid selected on the basis that it does not interfere with the sample being measured and wherein by increasing the dielectric constant of the predetermined dielectric material, beam waist radius decreases at higher frequencies so as to permit the usage of smaller sample sizes and to raise cut-off frequencies.

13. The method of claim 12 wherein the predetermined dielectric material is selected such that effective electrical spot size and microwave beam cross-section and cavity volume occupied by the resonating microwave decrease.

14. The method of claim 11 wherein the mirrors are confocal mirrors and the predetermined dielectric material is a liquid, wherein the sample moves through the liquid, and wherein the open cavity resonator assembly comprises a support for positioning of the sample within the dielectric liquid.

15. The method of claim 11 wherein the mirrors are one of spherical, cylindrical, curved, concave, or flat, and have a center of symmetry, and the dielectric material is one of a liquid, or gel, and wherein the sample is placed in the center of symmetry between the mirrors.

16. The method of claim 11 wherein the sample is movable throughout the liquid or gel predetermined dielectric material, and wherein usage of a predetermined dielectric material with a high dielectric constant reduces beam waist of the resonating microwave at resonant frequency mode enabling testing at higher frequencies.

17. The method of claim 16 wherein a predetermined dielectric material is used with a high dielectric constant in the range of 2 to 100,000 such that wavelength within the dielectric decreases which increases maximum wavelength and lowers cutoff frequency without affecting quality of the measurement of the sample.

18. The method of claim 14 wherein the open cavity resonator assembly is placed within an environmental chamber to enable dielectric properties of the sample to be determined as a function of temperature.

19. The method of claim 11 wherein the predetermined dielectric material is a liquid, wherein the sample moves through the liquid.

20. The method of claim 11 wherein the dielectric constant and loss tangent of the sample is measured from a resonance condition based upon a sample thickness.

* * * * *